(12) United States Patent
Brandvold

(10) Patent No.: US 10,519,079 B2
(45) Date of Patent: *Dec. 31, 2019

(54) LOW METAL BIOMASS-DERIVED PYROLYSIS OILS AND PROCESSES FOR PRODUCING THE SAME

(71) Applicant: UOP LLC, Des Plaines, IL (US)

(72) Inventor: Timothy A. Brandvold, Arlington Heights, IL (US)

(73) Assignee: UOP LLC, Arlington Heights, IL (US)

( * ) Notice: Subject to any disclaimer, the term of this patent is extended or adjusted under 35 U.S.C. 154(b) by 432 days.

This patent is subject to a terminal disclaimer.

(21) Appl. No.: 14/230,154

(22) Filed: Mar. 31, 2014

(65) Prior Publication Data

US 2014/0213833 A1 Jul. 31, 2014

Related U.S. Application Data

(62) Division of application No. 12/646,239, filed on Dec. 23, 2009, now Pat. No. 8,715,490.

(51) Int. Cl.
*C07C 2/12* (2006.01)
*C07C 7/12* (2006.01)

(52) U.S. Cl.
CPC ....................... *C07C 7/12* (2013.01)

(58) Field of Classification Search
CPC .. C07C 7/12; B01J 49/60; B01J 39/05; C10G 2300/1011; C10G 2300/205; C10G 2300/4018; C10G 2300/44; C10G 25/02
USPC ................. 585/16, 823, 14; 502/33
See application file for complete search history.

(56) References Cited

U.S. PATENT DOCUMENTS

| | | | | |
|---|---|---|---|---|
| 3,313,726 A * | 4/1967 | Campbell | ............ | B01J 49/0008 210/670 |
| 4,260,473 A * | 4/1981 | Bauer | .................... | C10G 1/045 201/2.5 |
| 4,460,458 A * | 7/1984 | Farcasiu | ................ | C10G 29/20 208/251 R |
| 6,080,696 A * | 6/2000 | Duke | ....................... | B01J 49/60 502/22 |
| 2001/0049451 A1 * | 12/2001 | Seidel | .................. | C07C 51/377 554/127 |
| 2003/0134015 A1 * | 7/2003 | Plaschke | ............... | A23B 4/048 426/234 |
| 2005/0004415 A1 | 1/2005 | Bull et al. | | |
| 2006/0111598 A1 | 5/2006 | Lin et al. | | |
| 2008/0035528 A1 * | 2/2008 | Marker | ..................... | C07C 4/04 208/113 |
| 2009/0253947 A1 * | 10/2009 | Brandvold | ............. | C10G 50/00 585/14 |
| 2009/0301930 A1 | 12/2009 | Brandvold et al. | | |

FOREIGN PATENT DOCUMENTS

GB 1517063 A 7/1978
WO 2011087676 A2 7/2011

OTHER PUBLICATIONS

Park, Y.-K.; Jeon, J.-K.; Kim, S.; Kim, J.-S. "Bio-oil from rice straw by pyrolysis using fluidized bed and char removal system", Prepr. Pap.-Am. Chem. Soc., Div. Fuel Chem (2004), 49, pp. 800-801.*
Oasmaa, A.; Czernik, S. "Fuel Oil Quality of Biomass Pyrolysis Oils-State of the Art for the End Users", Energy & Fuels (1999), 13, pp. 914-921.*
"Bio-oil—Pyrolysis Liquid"; pp. 1 and 2 (Oct. 1, 2002) (Year: 2002).*
Boucher, M. E. et. al. "Bio-oils obtained by vacuum pyrolysis of softwood bark as a liquid fuel for gas turbines. Part I: Properties of bio-oil and its blends with methanol and a pyrolytic aqueous phase", Biomass and Bioenergy, 19, (2000); pp. 337-350. (Year: 2000).*
Purolite, "Methanol washing of Purolite PD206 when used to remove glycerin in a dry biodiesel manufacturing facility", Application Notes, Puralite PD206 Guide, 2007.
Search Report dated Dec. 15, 2014 for corresponding EP Application No. EP 10 84 3485. The Search Report appears to be dated Dec. 8, 2014.

* cited by examiner

Primary Examiner — Sharon Pregler
(74) Attorney, Agent, or Firm — Paschall & Maas Law Office, LLC; James C. Paschall

(57) ABSTRACT

Low metal biomass-derived pyrolysis oils and processes for producing the same are provided. Low metal biomass-derived pyrolysis oil is produced by a process of contacting metal-containing biomass-derived pyrolysis oil with an acidic ion-exchange resin having sulfonic acid groups. Low metal biomass-derived pyrolysis oil is removed from spent acidic ion-exchange resin after ion-exchange.

10 Claims, 4 Drawing Sheets

LOW METAL BIOMASS-DERIVED PYROLYSIS OILS AND PROCESSES FOR PRODUCING THE SAME

CROSS-REFERENCE TO RELATED APPLICATIONS

This application is a Division of U.S. application Ser. No. 12/646,239 filed Dec. 23, 2009, the contents of which are hereby incorporated by reference in its entirety.

FIELD OF THE INVENTION

The present invention generally relates to biofuels and processes for producing biofuels, and more particularly relates to low metal biomass-derived pyrolysis oils and processes for producing the same.

DESCRIPTION OF RELATED ART

Fast pyrolysis is a process during which organic biomass materials, such as wood waste, agricultural waste, etc. are rapidly heated to about 450° C. to about 600° C. in the absence of air. Under these conditions, organic vapors, pyrolysis gases and ash (char) are produced. The vapors are condensed to biomass-derived pyrolysis oil. Biomass-derived pyrolysis oil can be burned directly as fuel for certain boiler and furnace applications, and can also serve as a potential feedstock in catalytic processes for the production of fuels in petroleum refineries. Biomass-derived pyrolysis oil has the potential to replace up to 60% of transportation fuels, thereby reducing the dependency on conventional petroleum and reducing its environmental impact.

However, biomass-derived pyrolysis oil is a complex, highly oxygenated organic liquid containing metals. The metals in the as-produced biomass-derived pyrolysis oil limit such commercial applications. Metals dissolved in the biomass-derived pyrolysis oil contribute to ash content of the oil upon combustion. It is desirable to reduce and minimize the ash content in the biomass-derived pyrolysis oil because such ash raises the total ash and particulate emissions when the biomass-derived pyrolysis oil is burned for consumption as a fuel. Environmental restrictions may limit such total emissions. In addition, when the biomass-derived pyrolysis oil is used as feedstock in catalytic processes to make transportation fuel, the metals in the oil foul downstream equipment and inhibit or deactivate the catalysts.

The removal of metal cations from biomass-derived pyrolysis oil to produce low metal biomass-derived pyrolysis oil is therefore important for utilization of biomass-derived pyrolysis oil as a biofuel. While ion-exchange resins are used to remove metals from aqueous solutions, they have not been effective in removing metals from biomass-derived pyrolysis oil because of their susceptibility to fouling. The oil will readily coat each ion-exchange bead and severely inhibit the bead's ability to adsorb ionic materials from the organic stream. As the oil is also sticky, it will result in agglomeration of the ion-exchange beads, producing channeling of the bed. The agglomeration can also significantly affect backwashing. While ion-exchange resins, if not too badly fouled, can be cleaned, conventional defouling activity requires an extremely labor intensive and costly process.

Accordingly, it is desirable to provide low metal biomass-derived pyrolysis oils and processes for producing the same. Furthermore, other desirable features and characteristics of the present invention will become apparent from the subsequent detailed description of the invention and the appended claims, taken in conjunction with the accompanying drawings and this background of the invention.

SUMMARY OF THE INVENTION

Processes are provided for reducing metals in metal-containing biomass-derived pyrolysis oil. In accordance with one exemplary embodiment, a process for reducing metals in the metal-containing biomass-derived pyrolysis oil comprises contacting the metal-containing biomass-derived pyrolysis oil with an acidic ion-exchange resin having sulfonic acid groups to produce low metal biomass-derived pyrolysis oil and spent ion-exchange resin. The low metal biomass-derived pyrolysis oil is removed from the spent ion-exchange resin.

Processes are provided for producing low metal biomass-derived pyrolysis oil in accordance with yet another exemplary embodiment of the present invention. The process comprises contacting metal-containing biomass-derived pyrolysis oil with an acidic ion-exchange resin having sulfonic acid active groups to form low metal biomass-derived pyrolysis oil and spent acidic ion-exchange resin. The low metal biomass-derived pyrolysis oil is removed from the spent acidic ion-exchange resin. The spent acidic ion-exchange resin is washed with a solvent selected from the group consisting of methanol, ethanol, acetone, and combinations thereof to remove at least a portion of residual low metal biomass-derived pyrolysis oil from the spent acidic ion-exchange resin and to retain residual solvent in the low metal biomass-derived pyrolysis oil.

Low metal biomass-derived pyrolysis oils produced by the processes are also provided in accordance with another exemplary embodiment of the present invention.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Various exemplary embodiments of the present invention are directed to a process for treating metal-containing biomass-derived pyrolysis oil (hereinafter "biomass-derived pyrolysis oil" or "starting oil") using acidic ion-exchange resins having sulfonic acid active groups that reduce the concentration of total metals in the starting oil. In general, the process removes alkali metals (sodium, potassium, and cesium) and alkaline earth metals (magnesium, calcium, and strontium) from the starting oil to prepare low-metal biomass-derived pyrolysis oils so that the oil is more suitable for use as biofuel. Transition metals (Fe, Ni, Mn) and other metals are also reduced. It should be appreciated that, while treated oil is generally described herein as a "low metal biomass-derived pyrolysis oil", "low metal biomass-derived pyrolysis oil" generally includes any treated oil having a lower total metal concentration as a result of the ion-exchange of the present invention than the concentration thereof in the starting biomass-derived pyrolysis oil stream.

The various embodiments of the process also selectively reduce metals without changing the other properties of the biomass-derived pyrolysis oil, which may otherwise result in a decrease in its suitability for use as a biofuel. Specifically, the low metal biomass-derived pyrolysis oil substantially retains the coloration, viscosity, carbon content, water content and acidity of the starting biomass-derived pyrolysis oil. In addition, the ion-exchange resin is not substantially fouled by the ion-exchange.

Figure 1:
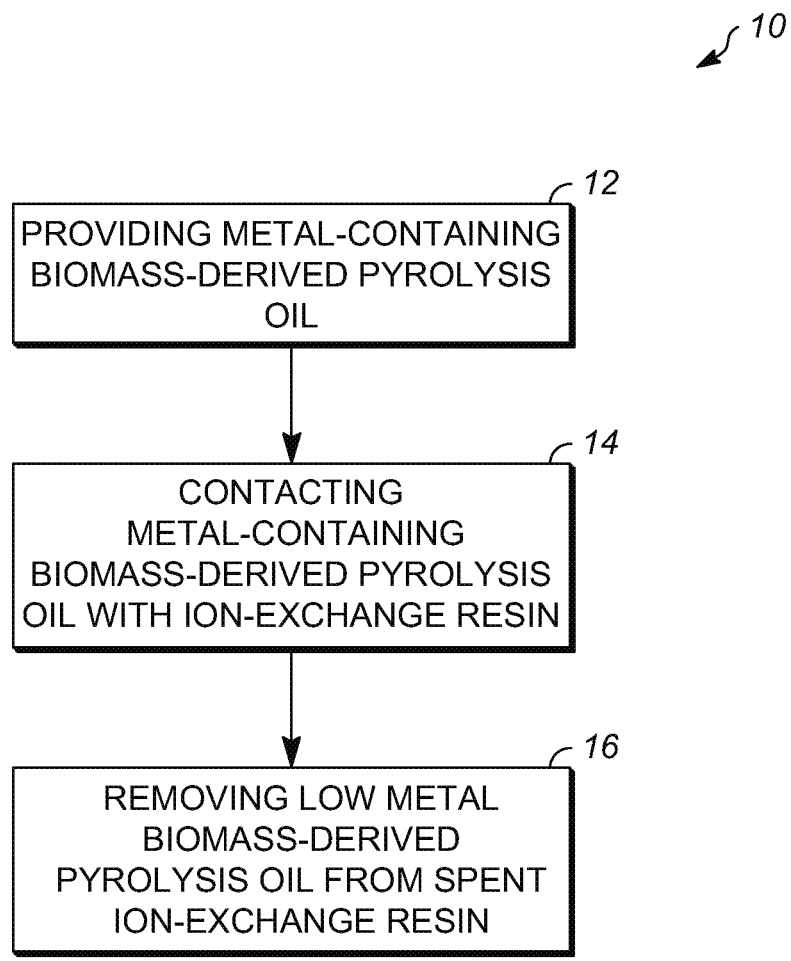
FIG. 1 is a flow chart of a process for producing low metal biomass-derived pyrolysis oils according to exemplary embodiments of the present invention.

As shown in FIG. 1, a process 10 for producing low metal biomass-derived pyrolysis oil begins by providing biomass-derived pyrolysis oil from a source such as a feed tank or other source operative to provide such biomass-derived pyrolysis oil (step 12). Pyrolysis oil composition is somewhat dependent on feedstock and processing variables. The total metal concentration in the biomass-derived pyrolysis oil generally ranges from about 0.02 weight percent (wt %) to about 0.5 weight percent (wt %) and typically contains alkali metals, alkaline earth metals, transition metals, and heavy metals. Metals are indigenous to all biomass and thus to the starting biomass-derived pyrolysis oil. Accordingly, the starting biomass-derived pyrolysis oil may alternatively be referred to herein as "metal-containing biomass-derived pyrolysis oil." Unless volatile under combustion conditions, these metals contribute to the ash content of the oil upon combustion. Biomass-derived pyrolysis oil is available from, for example, Ensyn Technologies Inc., of Ontario, Canada.

The biomass-derived pyrolysis oil may be produced, for example, from fast pyrolysis of wood biomass in a pyrolysis reactor. However, the invention is not so limited. Virtually any form of biomass can be considered for pyrolysis to produce biomass-derived pyrolysis oil. In addition to wood, biomass-derived pyrolysis oil may be derived from biomass material such as bark, agricultural wastes/residues, nuts and seeds, algae, grasses, forestry residues, cellulose and lignin, or the like. The biomass-derived pyrolysis oil may be obtained by different modes of pyrolysis, such as fast pyrolysis, vacuum pyrolysis, catalytic pyrolysis, and slow pyrolysis (also known as carbonization) or the like. The starting biomass-derived pyrolysis oil may be filtered by known filtering methods to remove solids to substantially prevent plugging of the ion-exchange resin.

Process 10 continues with contacting the biomass-derived pyrolysis oil stream, whether filtered or unfiltered, with an ion-exchange resin (step 14). The biomass-derived pyrolysis oil stream that contacts the ion-exchange resin undergoes ion-exchange such that metal ions are captured by the ion-exchange resin. More specifically, the ion-exchange resin contains sulfonic acid at its active sites. When the biomass-derived pyrolysis oil contacts the resin, the metals preferentially migrate out of the oil to the active sites on the ion-exchange resin. The metals in the biomass-derived pyrolysis oil are replaced by hydrogen ions.

The ion-exchange can be accomplished by either a batch method or a continuous column method. In the batch method, the ion-exchange resin and starting biomass-derived pyrolysis oil are contacted by mixing the resin and starting oil in a resin vessel, batch tank, or the like. A given weight of ion-exchange resin is added to a known volume of starting biomass-derived pyrolysis oil as hereinafter described. The amount of ion-exchange resin added to the fixed amount of oil is typically an excess of resin (based on theoretical resin capacity as defined below). The optimum resin to oil ratio is determined experimentally and is impacted by temperature and exposure time. The resin/oil mixture is agitated for about 0.5 hours to about 24 hours, preferably about 0.5 to about 4 hrs (hereinafter "the exposure time") at a temperature of about 10° C. to about 120° C., preferably from about 20° C. to about 60° C. Samples of the treated oil may be collected and analyzed for metal content as hereinafter described.

In the continuous column method, the ion-exchange resin and the biomass-derived pyrolysis oil are contacted by passing the biomass-derived pyrolysis oil through a column (of one or more "beds") containing the ion-exchange resin. The resin temperature may be from about 10° C. to about 120° C., preferably from about 20° C. to about 60° C. The biomass-derived pyrolysis oil is passed through the column by positive pressure flow or by gravity flow. When pressure is applied, the absolute pressure is from greater than 0 KPa to about 13790 KPa (0 to about 2000 psi), preferably from greater than 0 KPa to about 689.5 KPa (greater than 0 psi to about 100 psi), and most preferably from about 13.8 KPa to about 206.8 KPa (about 2 psi to about 30 psi). When no pressure is applied, the low-metal biomass-derived pyrolysis oil passes downward through the column and is allowed to slowly elute gravimetrically.

Figure 2:
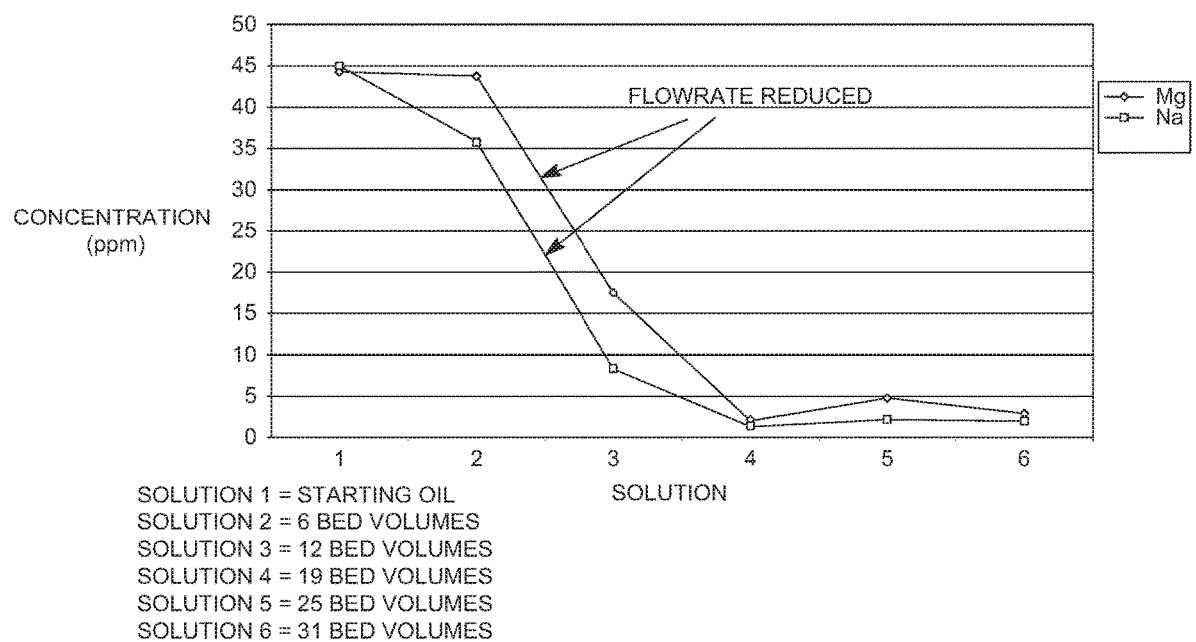
FIGS. 2-4 are plots illustrating the effect of Liquid Hourly Space Velocity (LHSV) (referred to in the figures as flow rate) reduction on removal of selected metal ions in various bed volumes of biomass-derived pyrolysis oil after gravimetric continuous column ion-exchange with Amberlyst® 36 ion-exchange resin at a temperature of about 25° C., in accordance with exemplary embodiments of the present invention.
Figure 3:
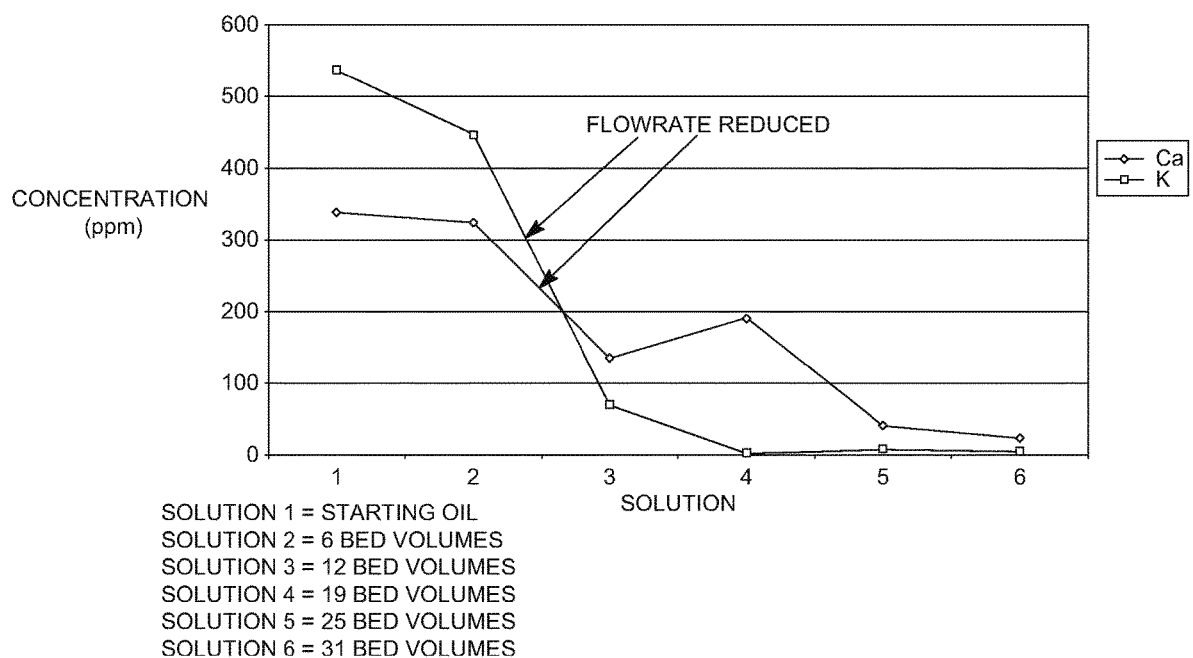
Figure 4:
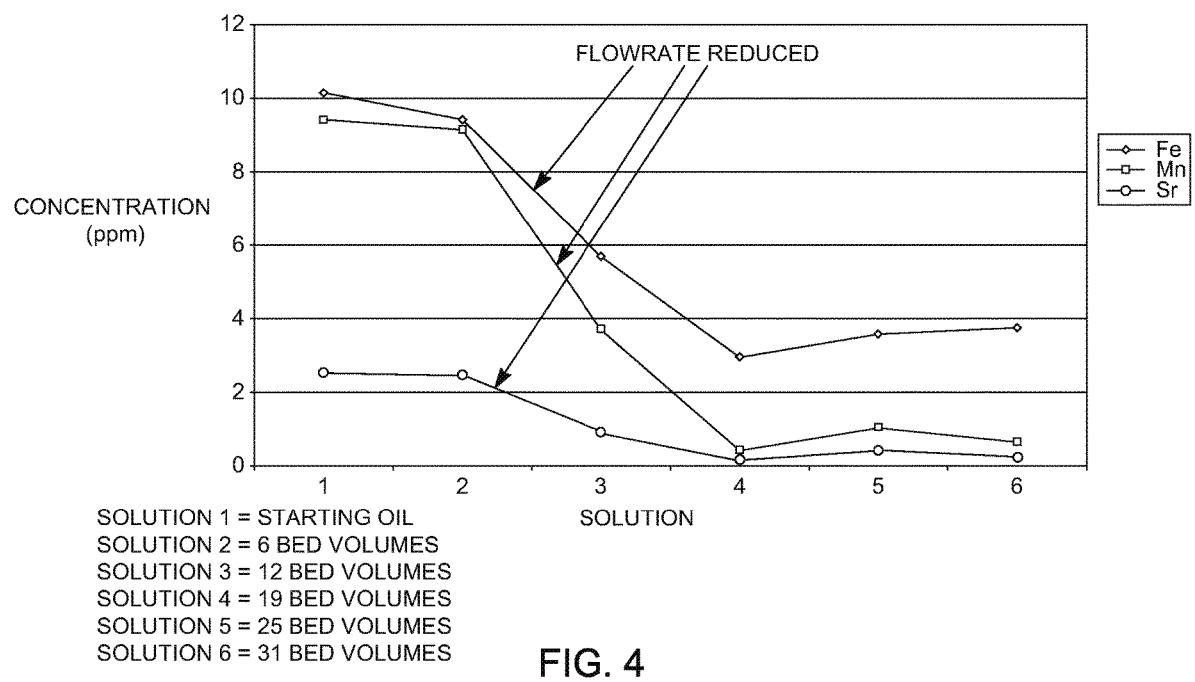

The biomass-derived pyrolysis oil is passed over the ion-exchange resin at a Liquid Hourly Space Velocity (LHSV) of about 0.1-20 hr$^{-1}$, preferably about 1-10 hr$^{-1}$. The faster the Liquid Hourly Space Velocity (LHSV), the less time there is for the ion-exchange. The relationship between Liquid Hourly Space Velocity (LHSV) and ion-exchange for a gravimetric continuous column ion-exchange is illustrated in FIGS. 2-4. FIGS. 2-4 are plots illustrating the effect of Liquid Hourly Space Velocity (LHSV) (referred to in the figures as flow rate) reduction on removal of selected metal ions in various bed volumes of biomass-derived pyrolysis oil after gravimetric continuous column ion-exchange with Amerlyst® 36 ion-exchange resin at a temperature of about 25° C. As evident from FIGS. 2-4, when the Liquid Hourly Space Velocity (LHSV) (flow rate) is reduced, the concentration of the selected metal ions in the treated oil is reduced significantly.

When metal levels in the treated biomass-derived pyrolysis oil reach a target concentration, or when metal concentration is constant (as determined by repeat measurements) over an extended time period, contact between the oil and the resin may be stopped and ion-exchange is deemed "complete". Metal concentrations in the oil may be measured by Atomic Absorption Spectroscopy (AAS), Inductively-Coupled Plasma-Atomic Absorption Spectroscopy (ICP-AAS) or other known methods.

The volume capacity of the ion-exchange resin ($VC_r$) for both batch and continuous column methods is the volume of resin needed to completely ion-exchange a given mass of oil and is determined by the equation:

$$VC_r \text{ (mL resin/kg oil)} = (\Sigma_i (C_i * 1000 \text{ g/kg})/MW_i) * V_i * 1000 \text{ meq/eq}/(TC_r * D_r)$$

wherein:

$C_i$ is the concentration of metal i in the biomass-derived pyrolysis oil in gram metal/gram oil;
$MW_i$ is the molecular weight of metal in g/mol;
$V_i$ is the valency (charge) of metal i in solution;
$D_r$ is the ion-exchange resin density in g/mL; and
$TC_r$ is the theoretical capacity of resin r. Theoretical capacity ($TC_r$) is often expressed in terms of milliequivalents ions/gram resin.

The maximum volume of oil (in liters) that can be processed per unit volume of ion-exchange resin in both batch and continuous column methods is expressed as:

$$V_{oil} = V_r / (VC_r * D_{feed})$$

wherein:

$V_{oil}$ is the volume of biomass-derived pyrolysis oil in liters;
$D_{feed}$ is the feed oil (the starting biomass-derived pyrolysis oil) density (in kilograms/liter);
$V_r$ is the resin volume in milliliters; and
$VC_r$ is the volume capacity of acidic ion-exchange resin to a given mass of metal-containing biomass-derived pyrolysis oil as determined above and expressed in mL resin/kg of biomass-derived pyrolysis oil. The $V_{oil}/V_r$ processed is also known as the number of bed volumes (BV) of oil processed. For a continuous column method, the volume of ion-exchange resin is fixed and a sub-theoretical volume of oil is passed through the ion-exchange resin. Metal-containing biomass-derived pyrolysis oil is contacted with about 0.1 to about 10 times the volume capacity ($VC_r$) of the acidic ion-exchange resin, preferably from about 1 to about 5 $VC_r$.

Using the various embodiments of the process 10, the total metal concentration is reduced, including the alkali metals such as sodium (Na), potassium (K) and cesium (Cs) as well as the alkaline earth metals, magnesium (Mg), calcium (Ca) and strontium (Sr). The transition metals, iron (Fe), manganese (Mn) and nickel (Ni), may also be reduced.

Resin efficiency, also referred to as ion-exchange efficiency ($IX_{eff}$), is defined as the fraction of metals removed from the liquid biomass-derived pyrolysis oil relative to the theoretical capacity of the resin and is determined as follows:

$$IX_{eff} = (\Sigma((C_{if} - C_{ip}) * V_i / MW_i * 1000 * M_f))) / (TC_r * M_r)$$

where $C_{if}$ and $C_{ip}$ are the concentration of metal i expressed in terms of grams of metal i per gram of oil in the feed (biomass-derived pyrolysis oil) and product (low metal biomass derived pyrolysis oil), respectively, $M_f$ is the mass of feed oil in grams, $MW_i$ is the molecular weight of metal i in g/mol, $V_i$ is the valency (charge) of metal i in solution, $TC_r$ is the theoretical capacity of resin r and $M_r$ is the mass in grams of resin r utilized. If it is assumed that a single metal ion neutralizes one resin exchange site regardless of ion charge, then the valance of the individual ions ($V_i$) is assigned as 1 for all metals. The higher the exchange efficiency, the better. Theoretical resin capacity multiplied by the ion exchange efficiency provides the actual capacity, which is the amount of ion-exchange resin needed to actually deionize a given amount of biomass-derived pyrolysis oil. The lower the experimental resin capacity, i.e., the lower the concentration of acid sites (eq/L), the larger the column needs to be, i.e., the greater the resin volume needed to deionize the biomass-derived pyrolysis oil.

Ion-exchange resins useful in the process according to exemplary embodiments of the present invention are strongly acidic cation-exchange resins. Preferably, the resin is used in the protonated form, i.e., all of the active groups are —SO$_3$H. Neutralized sulfonic acid resins, in which some or all of the protons have been exchanged by a cation such as lithium, sodium, potassium, magnesium, and calcium are also suitable. However, if resins are supplied with an alternate counterion (i.e., sodium, Na+), then the acid form may be generated prior to use by treatment with aqueous acid (such as hydrochloric, nitric, or sulfuric acid, etc.) This is commonly known in the art as ion-exchange resin activation. Preferably, the resin comprises sulfonated copolymers of styrene.

Preferred sulfonic acid resins for use in the method of the invention are macroreticular resins. As used herein, "macroreticular resins" are made of two continuous phases: a continuous pore phase and a continuous gel polymeric phase. The continuous gel polymeric phase is structurally composed of small spherical microgel particles agglomerated together to form clusters, which, in turn, form interconnecting pores. The surface area arises from the exposed surface of the microgel clusters. Macroreticular ion exchange resins can be made with different surface areas ranging from 7 to 1500 m$^2$/g, and average pore diameters ranging from about 5 to about 10000 nm.

Gel-type resins may also be used. As used herein, "gel-type resins" are generally translucent. There are no permanent pore structures for the gel-type resins. The pores are generally considered to be molecular-scale micropores. The pore structures are determined by the distance between the polymer chains and crosslinks which vary with the crosslink level of the polymer, the polarity of the solvent, and the operating conditions. Macroreticular resins are preferable for continuous column ion-exchange applications where resin swelling/shrinking should be minimized, while gel-type resins are preferred for batch ion-exchange applications, but either type may be used in either application.

Suitable acidic ion-exchange resins include those manufactured by Dow Chemical Co., Midland, Mich. (USA) under the tradenames/trademarks DOWEX® MARATHON C, DOWEX® MONOSPHERE C-350, DOWEX® HCR-S/S, DOWEX® MARATHON MSC, DOWEX® MONOSPHERE 650C, DOWEX® HCR-W2, DOWEX® MSC-1, DOWEX® HGR NG (H), DOWE® DR-G8, DOWEX® 88, DOWEX® MONOSPHERE 88, DOWEX® MONOSPHERE C-600 B, DOWEX® MONOSPHERE M-31, DOWEX® MONOSPHERE DR-2030, DOWEX® M-31, DOWEX® G-26 (H), DOWEX® 50W-X4, DOWEX® 50W-X8, DOWEX® 66, those manufactured by Rohm and Haas, Philadelphia, Pa. (USA) under the tradenames/trademarks Amberlyst® 131, Amberlyst® 15, Amberlyst® 16, Amberlyst® 31, Amberlyst® 33, Amberlyst® 35, Amberlyst® 36, Amberlyst® 39, Amberlyst® 40 Amberlyst® 70, Amberlite® FPC11, Amberlite® FPC22, Amberlite® FPC23, those manufactured by Brotech Corp., Bala Cynwyd, Pa. (USA) under the tradnames/trademarks Purofine® PFC150, Purolite® C145, Purolite® C150, Purolite® C160, Purofine® PFC100, Purolite® C100, those manufactured by Thermax Limited Corp., Novi, Mich. (USA) under the tradename/trademark Monoplus™ S100 and Tulsion® T42.

Referring again to FIG. 1, the low metal biomass-derived pyrolysis oil is then removed from the used ion-exchange resin (hereinafter the "spent ion-exchange resin") (step 16). In a batch ion-exchange, the low metal biomass-derived pyrolysis oil may be removed by filtration, decantation, or other known method. In continuous column ion exchange, the low metal biomass-derived pyrolysis oil is removed from the spent ion-exchange resin when the low metal biomass-derived pyrolysis oil elutes from the column gravimetrically or under positive pressure.

A portion of the low metal biomass-derived pyrolysis oil may remain on the spent ion-exchange resin when feed flow is stopped and low metal biomass-derived pyrolysis oil is removed from the spent ion-exchange resin. Any portion thereof that remains on the spent ion-exchange resin is referred to herein as "residual oil". At least a portion of the residual oil may be recovered by purging the ion-exchange column with gas such as nitrogen, air or the like. Alternatively, at least a portion of the residual oil may be recovered by washing the spent ion-exchange resin with about 1 to about 10 column volumes of a suitable solvent selected from the group consisting of methanol, ethanol, acetone, or combinations thereof. Small amounts of residual oil may remain on the ion-exchange resin and is therefore considered a loss. Any recovered low metal biomass-derived pyrolysis oil may be sent for further processing into biofuel. The recovered low metal biomass-derived pyrolysis oil may contain residual solvent, which may increase the storage stability of the low metal biomass-derived pyrolysis oil. It is known, for example, that the addition of ethanol to biomass-derived pyrolysis oil helps to keep the oil phase stable during storage.

From the foregoing, it is to be appreciated that the total metal concentration in the low metal biomass-derived pyrolysis oil may be reduced from that of the starting biomass-derived pryolysis oil to improve the suitability of the biomass-derived pyrolysis oil for use as a biofuel. In addition, other properties such as viscosity, carbon content, water content and acidity of the biomass-derived pyrolysis oil remain substantially unchanged after ion-exchange.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for producing low metal biomass-derived pyrolysis oil comprising the steps of:
    contacting metal-containing biomass-derived pyrolysis oil with an acidic ion-exchange resin having sulfonic acid active groups to form low metal biomass-derived pyrolysis oil and spent acidic ion-exchange resin;
    removing the low metal biomass-derived pyrolysis oil from the spent acidic ion-exchange resin; and
    washing the spent acidic ion-exchange resin with a solvent selected from the group consisting of methanol, ethanol, acetone, and combinations thereof to remove at least a portion of residual low metal biomass-derived pyrolysis oil from the spent acidic ion-exchange resin and to retain residual solvent in the residual low metal biomass-derived pyrolysis oil;
    processing the residual low metal biomass-derived pyrolysis oil and residual solvent retained in the residual low metal biomass-derived pyrolysis oil into biofuel.

2. The process of claim 1, wherein the step of contacting the metal-containing biomass-derived pyrolysis oil with the acidic ion-exchange resin comprises calculating the volume of ion-exchange resin to a given mass of metal-containing biomass-derived pyrolysis oil according to the following equation:

$$VC_r \text{ (mL resin/kg oil)} = (\Sigma_i(C_i*1000 \text{ g/kg})/MW_i)*V_i*1000 \text{ meq/eq}/(TC_r*D_r)$$

wherein:
    $VC_r$ is the volume capacity of the acidic ion-exchange resin to a given mass of metal-containing biomass-derived pyrolysis oil expressed in mL resin/kg of oil;
    $C_i$ is the concentration of metal i in the metal-containing biomass-derived pyrolysis oil in gram metal/gram oil;
    $MW_i$ is the molecular weight of metal i in g/mol;
    $V_i$ is the valency (charge) of metal i in solution;
    $TC_r$ is the theoretical capacity of the acidic ion-exchange resin r in milliequivalents ions/gram resin; and
    $D_r$ is the acidic ion-exchange resin density in g/mL.

3. The process of claim 2, wherein the step of contacting the metal-containing biomass-derived pyrolysis oil with the acidic ion-exchange resin comprises calculating the maximum volume ($V_{oil}$) of metal-containing biomass-derived pyrolysis oil per unit volume of resin that can be ion-exchanged according to the equation:

$$V_{oil} = V_r/(VC_r*D_{feed})$$

wherein:
    $V_{oil}$ is the volume of metal-containing biomass-derived pyrolysis oil in liters;
    $D_{feed}$ is the density of the metal-containing biomass-derived pyrolysis oil in kilograms/liter;
    $V_r$ is the acidic ion-exchange resin volume in milliliters; and
    $VC_r$ is the volume capacity of the acidic ion-exchange resin to a given mass of metal-containing biomass-derived pyrolysis oil expressed in mL resin/kg of oil.

4. The process of claim 3, wherein the step of contacting the metal-containing biomass-derived pyrolysis oil comprises contacting the metal-containing biomass-derived pyrolysis oil with about 0.1 to about 10 times the volume capacity ($VC_r$) of the acidic ion-exchange resin.

5. The process of claim 1, wherein the step of contacting the metal-containing biomass-derived pyrolysis oil with the acidic ion-exchange resin comprises mixing the acidic ion-exchange resin with the metal-containing biomass-derived pyrolysis oil.

6. The process of claim 5, wherein the step of contacting the metal-containing biomass-derived pyrolysis oil comprises contacting the metal-containing biomass-derived pyrolysis oil with the acidic ion-exchange resin at:
    a temperature of about 10° C. to about 120° C. and an exposure time of about 0.5 hours to about 24 hours.

7. The process of claim 1, wherein the step of contacting the metal-containing biomass-derived pyrolysis oil with the acidic ion-exchange resin comprises the step of passing the metal-containing biomass-derived pyrolysis oil through a column containing the acidic ion-exchange resin.

8. The process of claim 7, wherein the step of contacting the metal-containing biomass-derived pyrolysis oil with the acidic ion-exchange resin comprises contacting at:
    a Liquid Hourly Space Velocity (LHSV) of about 0.1 to about 20 hr$^{-1}$, and
    a temperature of about 10° C. to about 120° C.

9. The process of claim 8, wherein the step of contacting the metal-containing biomass-derived pyrolysis oil with the acidic ion-exchange resin further comprises contacting at an absolute pressure of greater than 0 KPa to about 13790 KPa (greater than 0 psi to about 2000 psi).

10. The process of claim 1 wherein the metal-containing biomass-derived pyrolysis oil comprises about 0.02 to about 0.5 weight percent metals.

\* \* \* \* \*